United States Patent [19]
Sweeney et al.

[11] Patent Number: 5,599,318
[45] Date of Patent: Feb. 4, 1997

[54] NEEDLE SHIELD ASSEMBLY HAVING A RELEASABLE LOCK

[75] Inventors: Niall Sweeney; Adriano Morigi, both of Rutherford; Sandor Gyure, West Orange, all of N.J.

[73] Assignee: Becton, Dickinson and Company, Franklin Lakes, N.J.

[21] Appl. No.: 520,523

[22] Filed: Aug. 29, 1995

[51] Int. Cl.$^6$ .................................................. A61M 5/00
[52] U.S. Cl. ........................... 604/263; 604/192; 128/919
[58] Field of Search .................................. 604/263, 187, 604/192, 110; 128/919

[56] References Cited

U.S. PATENT DOCUMENTS

| | | | |
|---|---|---|---|
| 3,658,061 | 4/1972 | Hall | 128/214.4 |
| 4,664,259 | 5/1987 | Landis | 206/365 |
| 4,838,871 | 6/1989 | Luther | 604/192 |
| 4,872,552 | 10/1989 | Unger | 206/365 |
| 4,886,503 | 12/1989 | Miller | 604/192 |
| 4,909,792 | 3/1990 | Norelli | 604/192 |
| 4,976,699 | 12/1990 | Gold | 604/192 |
| 4,982,842 | 1/1991 | Hollister | 206/365 |
| 5,055,102 | 10/1991 | Sitnik | 604/192 |
| 5,116,325 | 5/1992 | Paterson | 604/192 |
| 5,135,509 | 8/1992 | Olliffe | 604/192 |
| 5,151,089 | 9/1992 | Kirk, III et al. | 604/192 |
| 5,188,611 | 2/1993 | Orgain | 604/192 |
| 5,197,954 | 3/1993 | Cameron | 604/110 |
| 5,232,454 | 8/1993 | Hollister | 604/192 |
| 5,232,455 | 8/1993 | Hollister | 604/192 |
| 5,242,417 | 9/1993 | Paudler | 604/192 |
| 5,312,369 | 5/1994 | Arcusin et al. | 604/192 |
| 5,445,619 | 8/1995 | Burns | 604/263 X |
| 5,462,534 | 10/1995 | Debreczeni | 604/192 |

*Primary Examiner*—John D. Yasko
*Attorney, Agent, or Firm*—John L. Voellmicke

[57] ABSTRACT

A needle shield assembly having a releasable lock of the present invention includes a needle cannula and a hub having a proximal end for connecting to a medical instrument and a distal end connected to the proximal end of the needle cannula. A base member is connected to the hub and includes a deflectable locking arm having a latch surface. A needle shield is hingedly connected to the base member. The needle shield includes a longitudinal opening therein and is capable of rotating back and forth between a first needle protecting position wherein the needle cannula is within the longitudinal opening of the needle shield and a second position exposing at least the distal end of the needle cannula. The needle shield includes a latch surface positioned to engage the latch surface of the base member when the needle shield is in the first position for locking the needle shield in the first position. The needle shield includes an activating member movably connected to the needle shield having an outwardly facing finger pad and a tip portion. The activating member is positioned so that digital pressure applied to the finger pad causes the tip portion of the activating member to push against the locking arm of the base member and deflect the locking arm so that the latch surface of the locking arm disengages the latch surface of the needle shield and so that continued digital pressure on the finger pad causes the needle shield to rotate from the first position to the second position.

21 Claims, 12 Drawing Sheets

NEEDLE SHIELD ASSEMBLY HAVING A RELEASABLE LOCK

FIELD OF THE INVENTION

The subject invention relates to needle shields for hypodermic needles, collection needles, catheter needles and other medical implements to help prevent accidental needle sticks.

DESCRIPTION OF THE PRIOR ART

Accidental needle sticks with a new unused needle can cause injury and render the needle unfit for further use. Accidental needle sticks with a used needle can transmit disease. As a result, most prior art needle assemblies have a needle shield. Some prior art needle shields define a rigid sleeve that can be telescoped over a needle cannula. This procedure requires a healthcare worker to hold the needle cannula and the associated medical implement in one hand and the shield in the other. Some medical procedures require the application of pressure to the penetration site after the needle has been removed. Thus, healthcare workers are often unable to use both hands for shielding the needle cannula. In these situations, workers merely deposit the used medical implement on a nearby surface with the intention of shielding at a more convenient time. However, until the needle is shielded or properly disposed of it presents a potential danger to other people. In some medical situations it is also desirable to be able to unshield the needle cannula using a one-hand procedure. Telescoping needle shields which are capable of shielding and unshielding a needle cannula require a two-hand procedure.

A needle shield which is hinged near the base of the needle has the advantage of allowing one handed needle reshielding. Thus providing the opportunity for immediate reshielding, under most circumstances, immediately after use. However, pivotable needle shields still require a two-handed procedure to unshield the needle. Also, the reshielding procedure requires the healthcare worker to place his or her hand close to the needle tip in order to grasp the needle shield and rotate it out of the needle shielding position. This procedure also creates the possibility of accidental needle contamination by inadvertent contact with the healthcare worker's hand. Further, pivoting needle shields which lock usually contain deflectable members in the needle shield which engage the needle upon shielding and prevent subsequent unshielding of the needle because the needle is trapped within the needle shield. Further attempts to rotate the shield out of the needle shielding position will bend the cannula but not expose it.

Another prior art hinged needle shield has a rotating cylinder with a longitudinal slot which is normally aligned with the slot in the needle shield. After the needle shield is rotated into the needle shielding position, the cylinder is rotated to occlude the longitudinal opening of the needle shield and trap the needle therein. This locking procedure allows subsequent unlocking but again requires a two-handed procedure.

As mentioned above, many prior art self-contained needle shield assemblies lock permanently in place once the needle is shielded for the first time. Accordingly, once the needle is used for filling through a medication vial having a pierceable stopper, it must be transported to the injection site unshielded. Under these circumstances, it is believed that a needle shield which can expose the needle for filing the hypodermic syringe and then locked into a needle shielding position and which can later be unlocked to expose the needle for injection into the patient is a desirable feature because the needle will be protected from contamination and damage between the time the syringe is filled and the time the injection is administered. It is also desirable that the unlocking of the needle shield be a one-handed operation which does not place the user's hand in proximity to the bare cannula.

Although the prior art provides many improved needle shield devices, there is still a need for a self-contained needle shield assembly wherein the needle shield can be positioned in a needle shielding position or a needle exposing position using a one-handed procedure. There is also a need for a self-contained needle shield assembly which automatically locks the needle shield when it is positioned in the needle protecting position, but allows subsequent single-handed unlocking of the shield to move it to a needle exposing position.

SUMMARY OF THE INVENTION

A needle shield assembly having a releasable lock of the present invention includes a needle cannula having a proximal end, a distal end and a lumen therethrough, and a hub having a proximal end for connecting to a medical instrument and a distal end connected to the proximal end of the needle cannula. A base member is connected to or formed integrally with the hub and includes a deflectable locking arm having a latch surface. An elongate needle shield is hingedly connected to the base member so that the needle shield can rotate about an axis which is transverse to the longitudinal axis of the needle cannula. The needle shield includes a longitudinal opening therein and is capable of rotating back and forth between a first needle protecting position wherein the needle cannula is within the longitudinal opening of the needle shield to a second position exposing at least the distal end of the needle cannula. The needle shield includes a latch surface positioned to engage the latch surface of the base member when the needle shield is in the first needle protecting position for locking the needle shield in the first position. The needle shield includes an activating member movably connected to the needle shield having an outwardly facing finger pad and a tip portion. The activating member is positioned so that digital pressure applied to the finger pad causes the tip portion of the activating member to push against the locking arm of the base member and deflect the locking arm so that the latch surface of the locking arm disengages the latch surface of the needle shield and so that continued digital pressure on the finger pad causes the needle shield to rotate toward the side of the needle shield containing the finger pad from the first needle shielding position to the second needle exposing position. The deflectable locking arm and the needle shield are configured so that rotation of the needle shield from the second position to the first position causes the latch surface of the locking arm and the latch surface of the needle shield to engage to lock the needle shield in the first position.

DETAILED DESCRIPTION

While this invention is satisfied by embodiments in many different forms, there are shown in the drawings and will be herein described in detail preferred embodiments of the invention with the understanding that the present disclosure is to be considered exemplary of the principles of the invention and is not intended to limit the scope of the invention to these embodiments illustrated. The scope of the invention will be measured by the appended claims and their equivalents.

Adverting to FIGS. 1–14, a needle shield assembly having a releasable lock such, as needle shield assembly 20, includes a needle cannula 21 having a proximal end 22, a distal end 23 and a lumen 25 therethrough defining a longitudinal axis 24. In this embodiment, the distal end of the needle cannula includes sharpened tip 26. It is within the purview of the present invention to include blunt cannula which are cannula without sharp tips. Blunt cannula are known in the art and are usually used to inject liquid into an I.V. set or other fluid flow path having an access port with a pre-slit septum. The blunt cannula is forced through the slit in the septum and into fluid communication with the fluid flow path. Upon removal of the blunt cannula the slit portion of the septum automatically seals itself.

A hub 28 includes a proximal end 29 and a distal end 31 connected to proximal end 22 of the needle cannula. A base member 32 is connected to the hub. There are many ways to join the base member to the hub such as through an interference fit, adhesives, ultrasonic welding and the like. It is within the purview of the present invention to include a hub and base member which are a unitary one-piece structure. The one-piece structure may be accomplished by many methods including injection molding the hub and base member as a one-piece unit thereby eliminating the need to assemble the base member to the hub during the manufacturing process.

An elongate needle shield 35 includes proximal end 37 hingedly connected to base member 32. In this embodiment, the hinge connection is accomplished by hinge holes 38 in parallel spaced arms 33 of the needle shield which engage opposed circular hinge pins 33 on base member 32 to allow the needle shield to rotate about an axis which is preferably transverse to the longitudinal axis of the needle cannula. Needle shield 35 also includes distal end 40 and longitudinal opening 41 which ends at the distal end of the needle shield at end wall 44.

Figure 1:
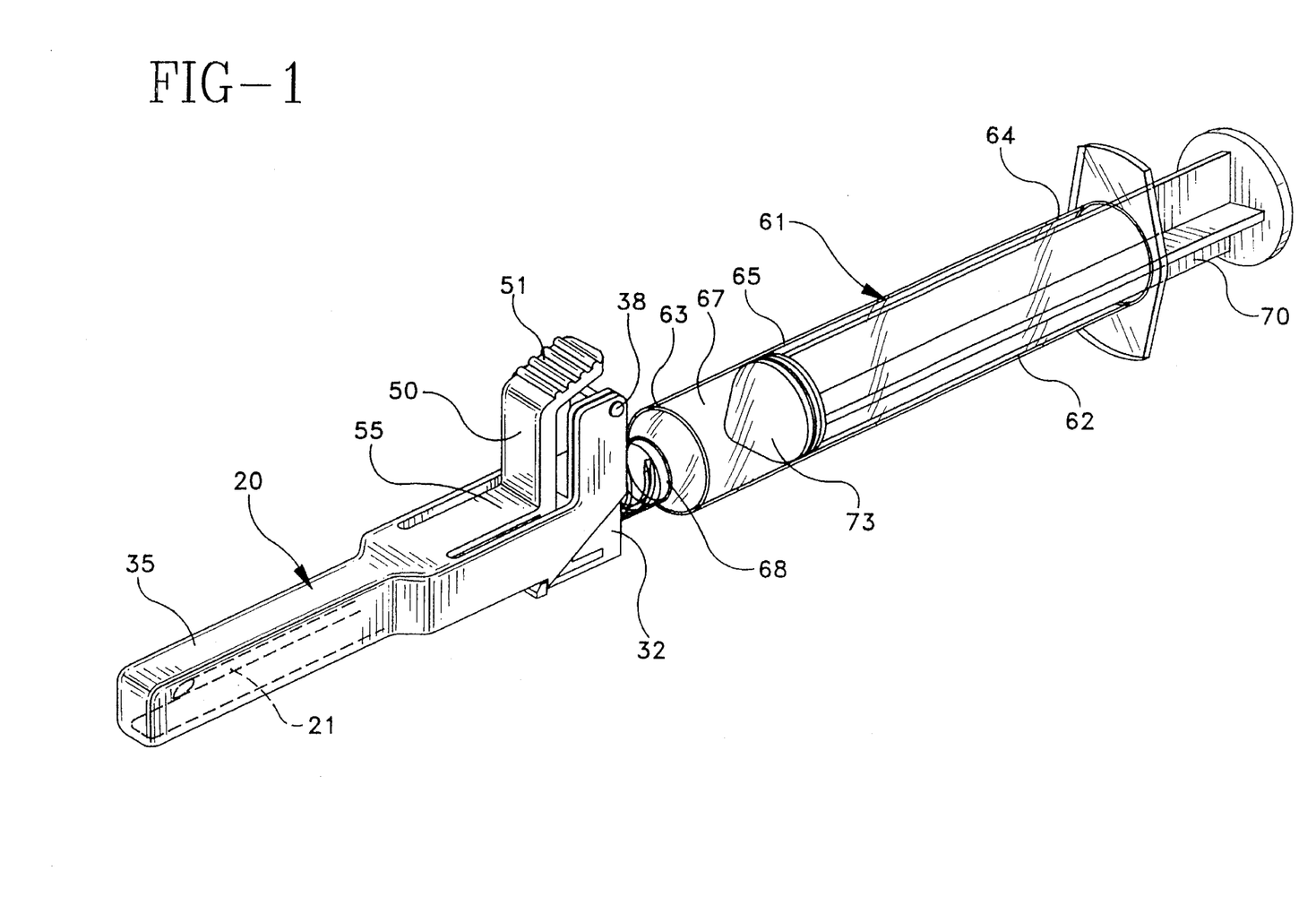
FIG. 1 is a perspective view of the needle shield assembly having a releasable lock, attached to a hypodermic syringe.
Figure 3:
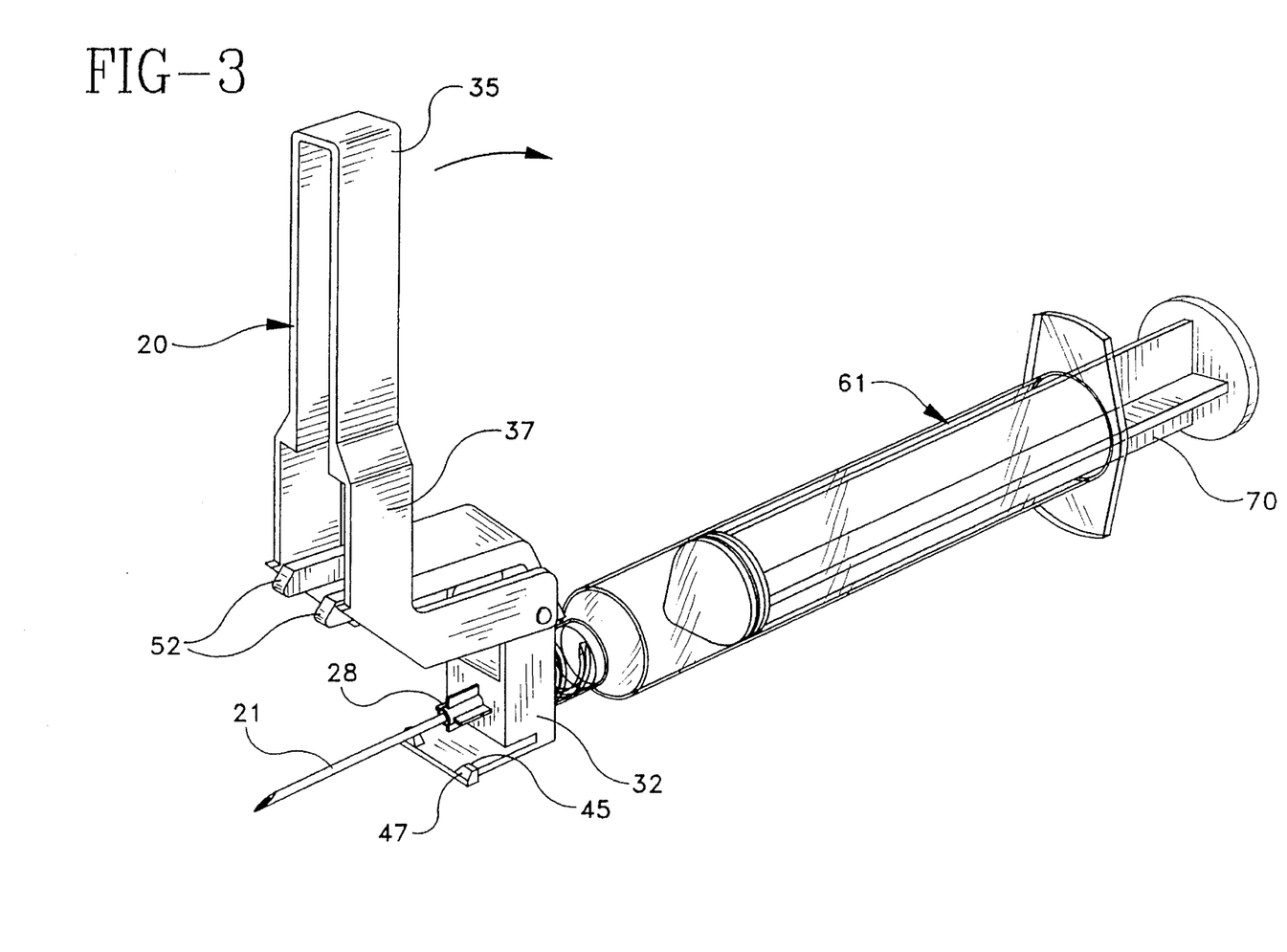
FIG. 3 is the needle shield assembly of FIG. 1 illustrating the needle shield at a needle exposing position.
Figure 4:
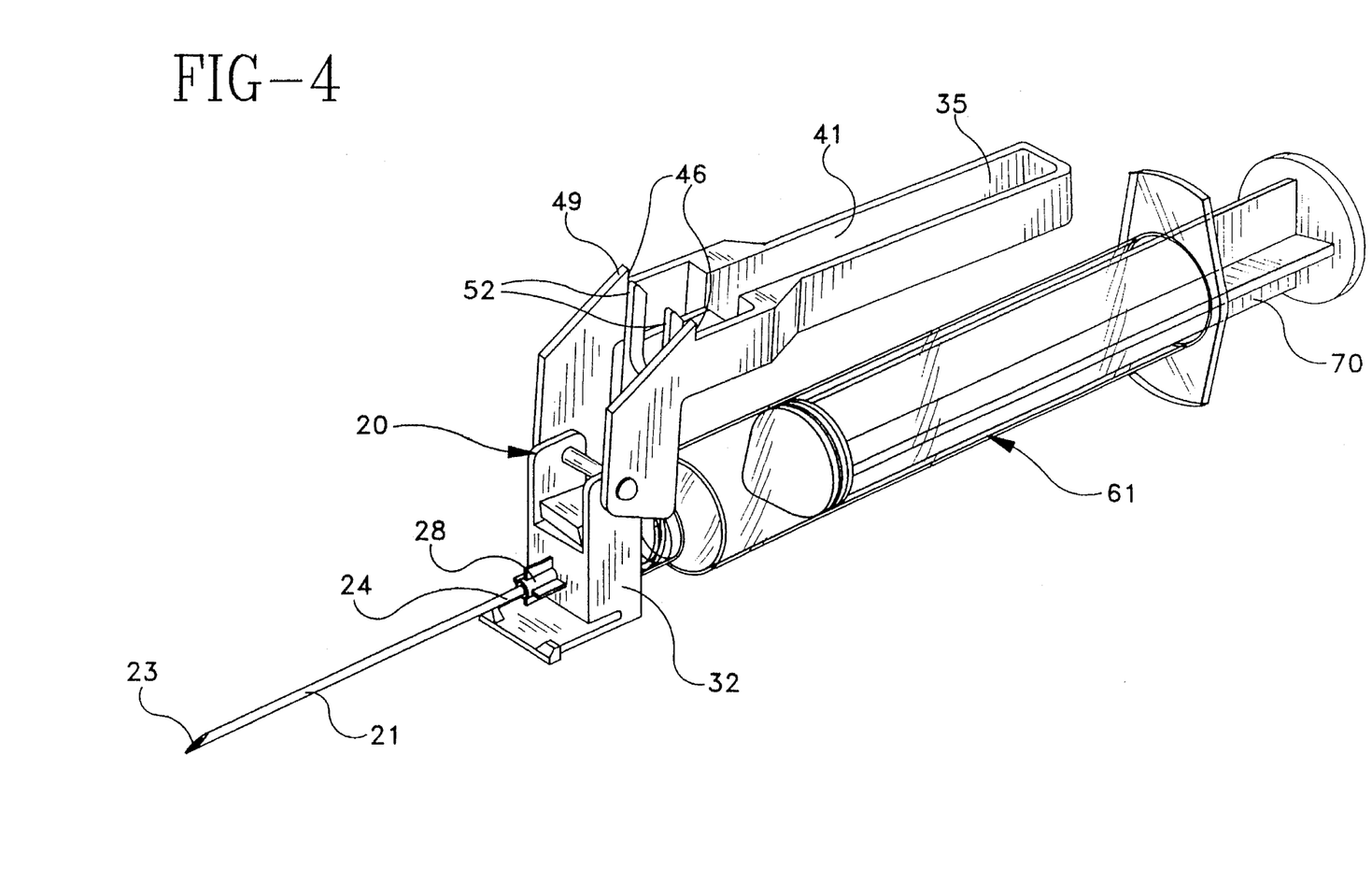
FIG. 4 is the needle shield assembly of FIG. 1 illustrating the needle shield and another needle exposing position.
Figure 5:
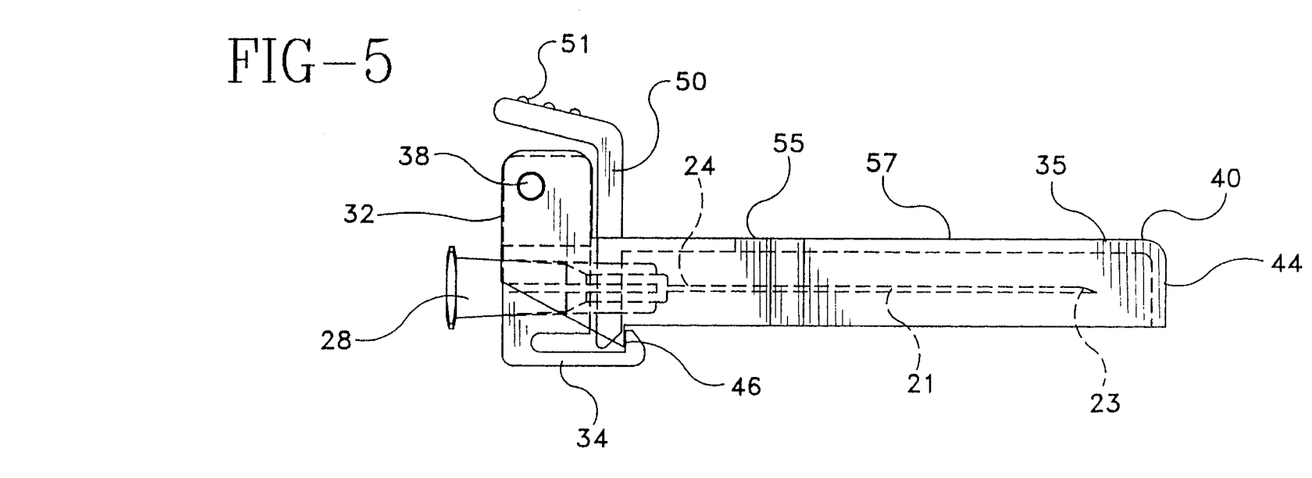
FIG. 5 is a side elevation view of the needle shield assembly of the present invention.

Needle shield 35 is capable of rotating back and forth between a first needle protecting position, as illustrated in FIG. 1 wherein needle cannula 21 is within longitudinal opening 41 of the needle shield, to a second position, such as the positions illustrated in FIGS. 3 and 4, exposing at least distal end 23 of the needle cannula.

Base member 32 includes a deflectable locking arm 34 having a latch surface 45. Also, needle shield 35 includes a latch surface 46 positioned to engage latch surface 45 on the base member when the needle shield is in a first needle protecting position for locking the needle shield in the first position. It is an important feature of the present invention that when the needle shield is rotated from the second position to the first position, latch surfaces 45 and 46 engage to lock the needle shield in the first position. Thus, the needle shield is not frictionally held in the first position but locked therein so that the needle shield cannot be rotated to expose the needle under normal operating conditions unless the latching surfaces are intentionally unlocked as will be explained in more detail hereinafter. In the preferred embodiment, surfaces 47 on the deflectable arm and surfaces 49 on the needle shield are configured so that rotation of the needle shield from the second position to the first position causes the latch surfaces of the latch arm and the locking surfaces of the needle shield to engage and lock the needle shield in the first position.

Figure 6:
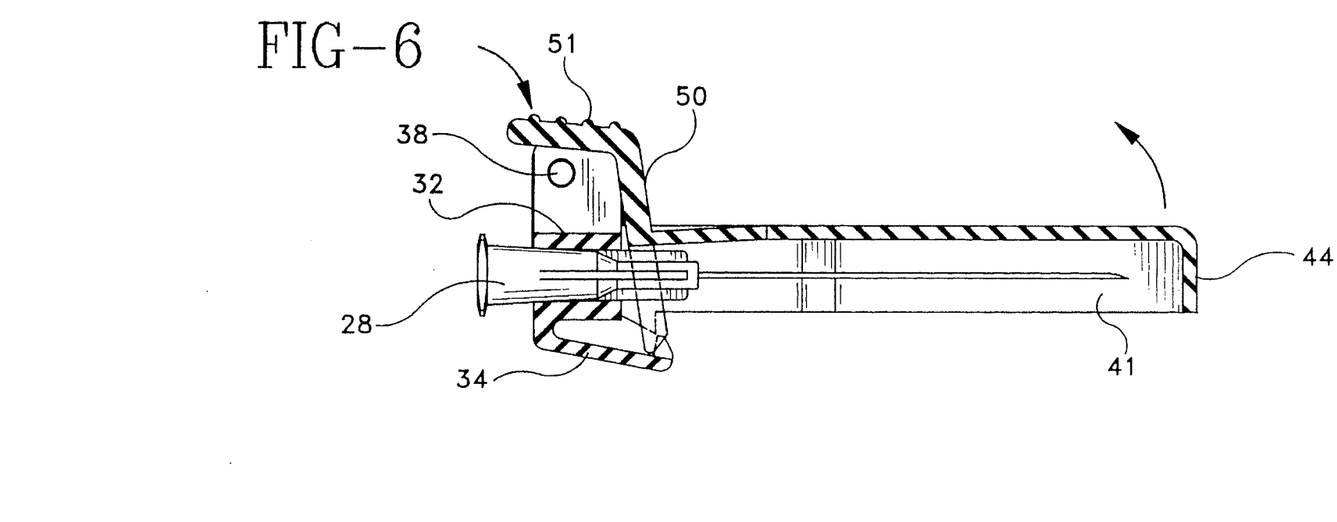
FIG. 6 is a partially cross-sectioned side elevation view of the needle shield assembly of FIG. 5 illustrating the interaction between the activating member and the base member to unlock the needle shield.
Figure 7:
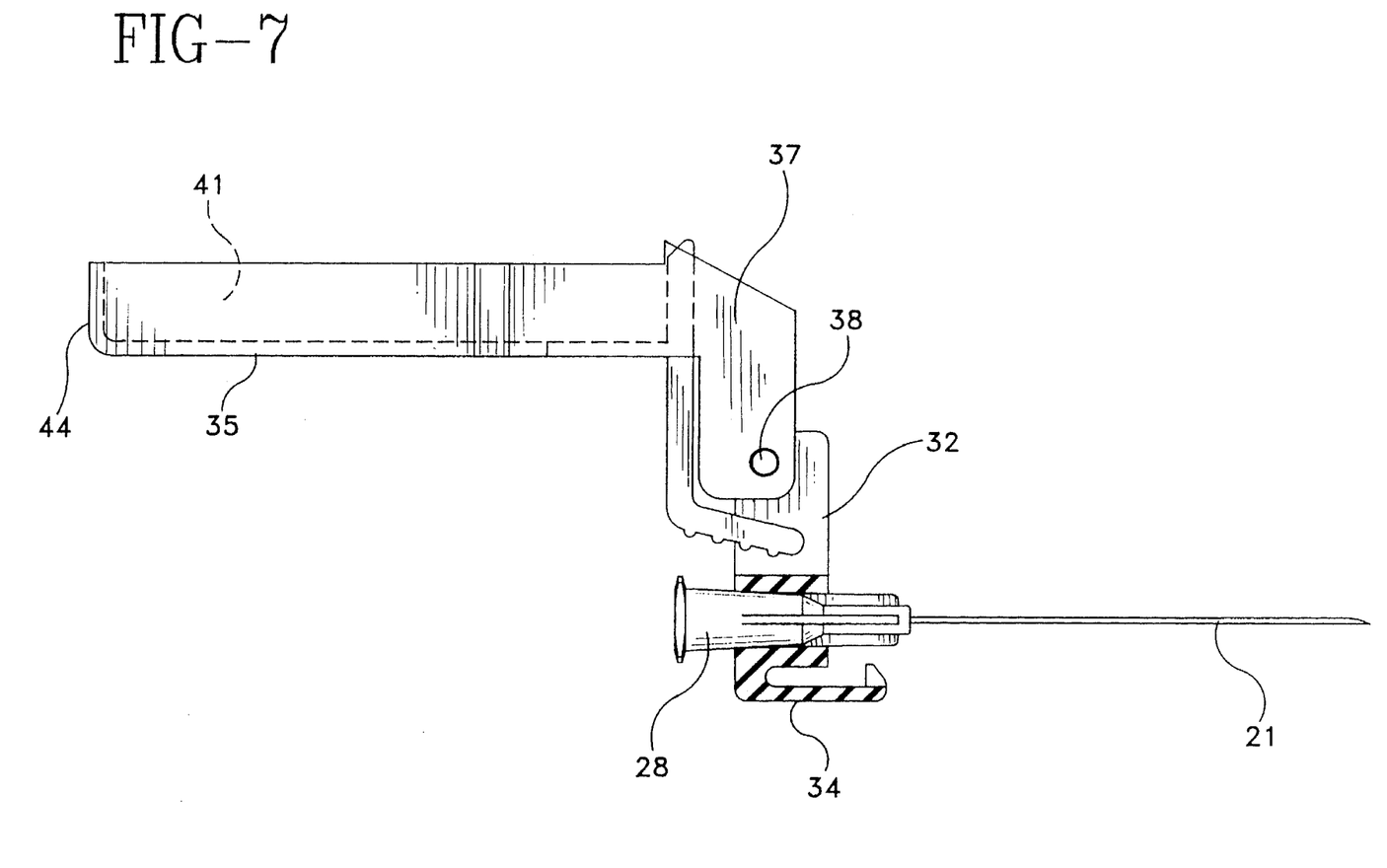
FIG. 7 is the needle shield assembly of FIG. 5 with the needle cannula exposed.
Figures 8, 9, 10:
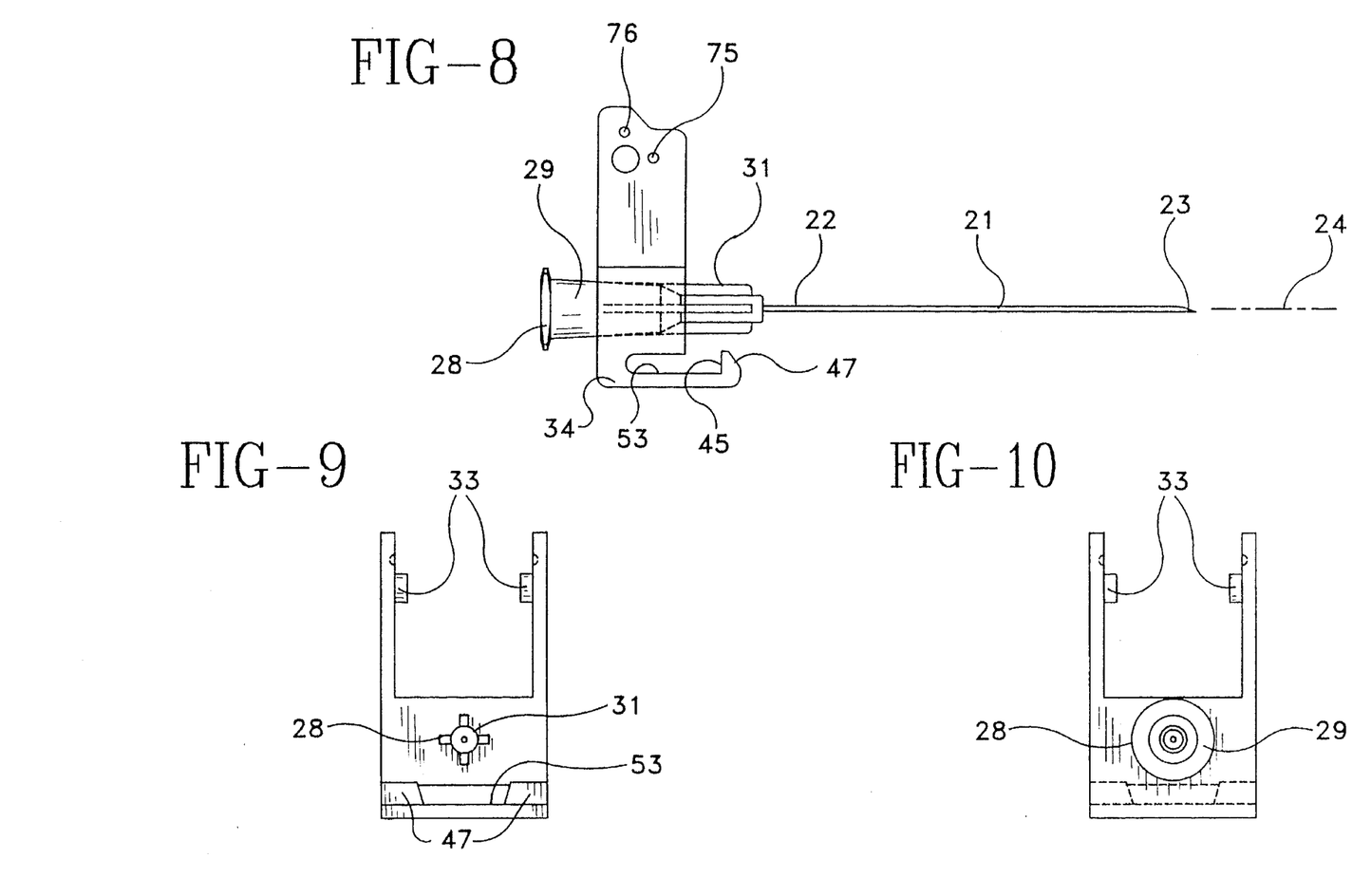
FIG. 8 is a side elevation view of the assembly of the needle cannula, hub and base member of the present invention.
FIG. 9 is a top elevational view of the assembly of FIG. 8.
FIG. 10 is a bottom elevational view of the assembly of FIG. 8.
Figure 11:
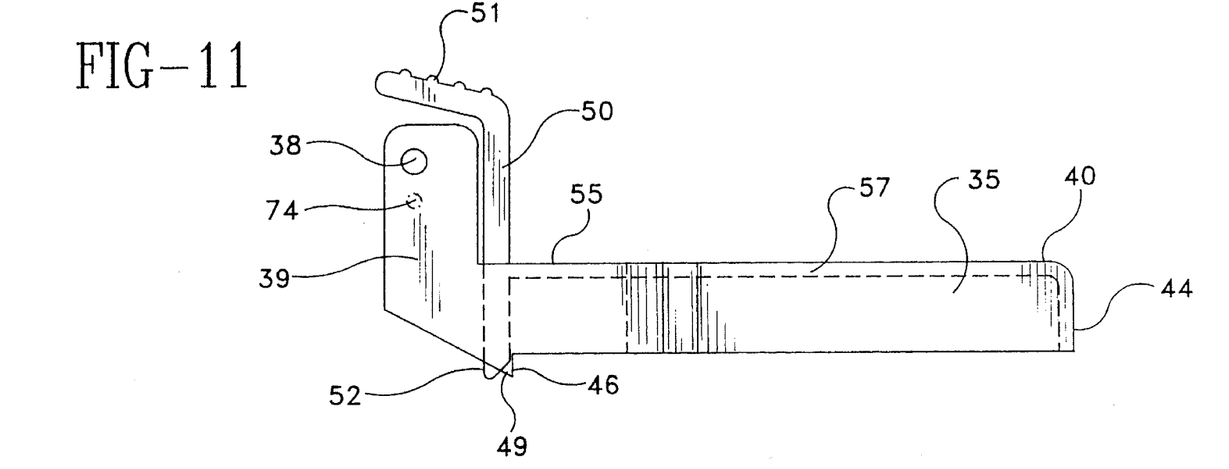
FIG. 11 is a side elevational view of the needle shield assembly of the present invention.
Figure 12:
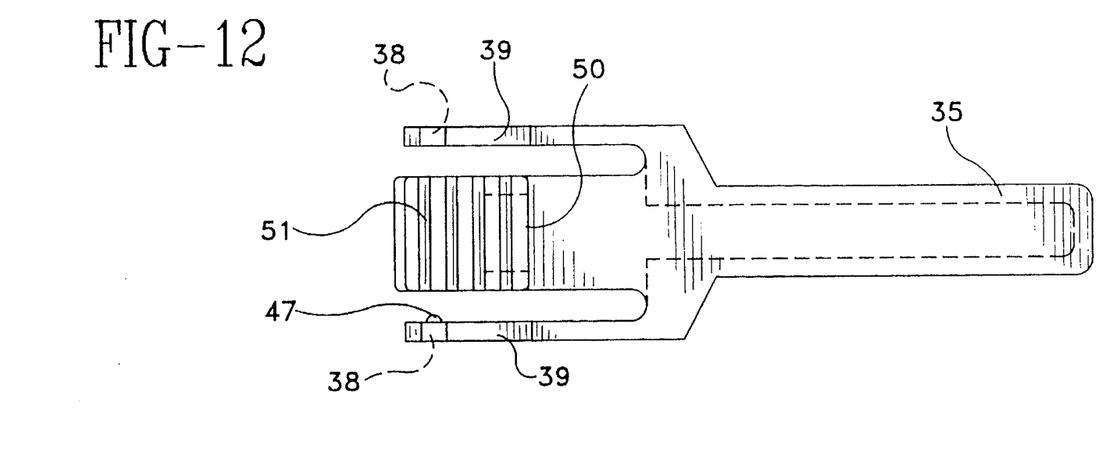
FIG. 12 is a left-side elevational view of the needle shield of FIG. 11.
Figure 13:
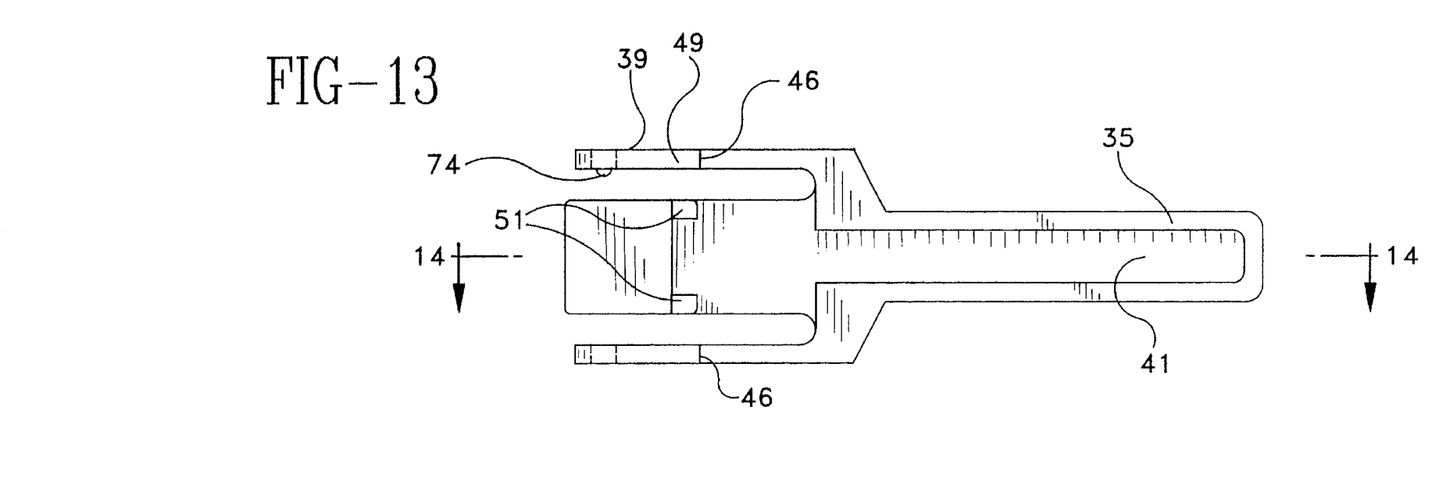
FIG. 13 is a right-side elevational view of the needle shield of FIG. 11.
Figure 14:
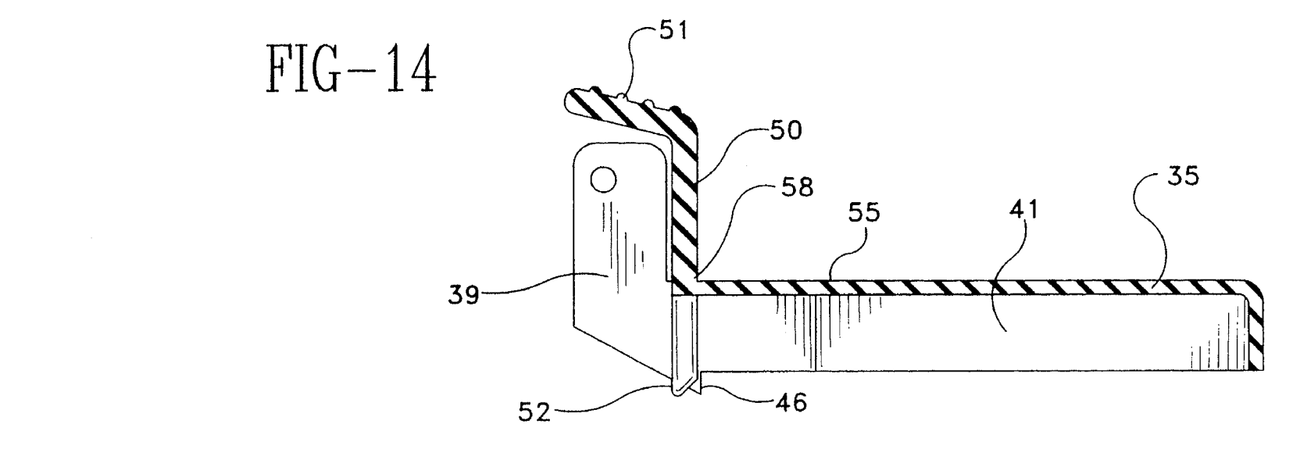
FIG. 14 is a cross-sectional view of the needle shield of FIG. 13 taken along lines 14—14.

Needle shield 35 further includes an activating member 50 movably connected to the needle shield having an outwardly facing finger pad 51 and a tip portion 52 preferably located on the opposite side of the needle cannula from the finger pad when the needle shield is in the first needle protecting position. The activating member is positioned so that digital pressure applied to the finger pad causes the tip portion of the activating member to push against locking arm at contact surface 53 of the locking arm, and deflect the locking arm, as illustrated in FIG. 6, so that latch surface 45 of the locking arm disengages latch surface 46 of the needle shield and so that continued digital pressure on the finger pad causes the needle to rotate toward the side of the needle shield containing the finger pad from the first needle shielding position to the second needle exposing position, as illustrated in FIGS. 2, 3, 4 and 7. This is an important feature of the present invention since the user can unlock the needle shield and rotate it from the first needle protecting position with a single-handed procedure comprising applying digital pressure to finger pad 51 of activating member 50. The unlocking and rotation of the needle shield is accomplished in one step with one finger motion. Without intentional deflection of the activating member the needle will remain safely locked within the needle shield, not to be re-exposed, under normal use, without the intentional act of the user. The needle shield is safely locked in a shielded position to prevent accidental inadvertent re-exposure of the needle cannula. The act of unlocking and rotating the needle shield out of the needle protecting position takes place by applying digital pressure on the opposite side of the needle from the longitudinal slot keeping the user's fingers on the opposite side of the needle from the slot helps prevent incidental contact with the needle during the procedure of exposing the needle cannula. The increased safety of having a securely locked needle shield and the ability to unlock and rotate the needle shield from a remote location away from the open side of the needle shield are important features that overcomes many of the shortcomings of the prior art.

The movable relationship between the activating member and the needle shield can be accomplished by many structures including various shapes and configurations of structure or mechanism connecting the elements such as linkages, concentric sliding structure, living hinges, separate hinges, and the like. In this embodiment, the movable relationship is a rotational relationship between the needle shield and the activating member which is achieved through a proximally directed cantilever arm 55 connected to the needle shield at location 57 so that it pivots therefrom as a cantilever beam. Free end 58 of cantilever arm 55 connects directly to activating member 50 so that when digital pressure is applied to the finger pad 51, cantilever arm 55 pivots or deflects toward deflectable locking arm 34 of the base member causing tip portion 52 to press against contact surface 53 on the locking arm to disengage latch surface 45 and latch surfaces 46. This action is best illustrated in FIG. 6.

For the purpose of illustration needle shield assembly 20 is connected to a hypodermic syringe 61 comprising a syringe barrel 62 having a distal end 63 and a proximal end 64 and a circular side wall 65 therebetween defining a chamber 67 for retaining fluid. The distal end of the syringe barrel is connected to the hub so that lumen 25 of the needle cannula is in fluid communication with chamber 67 of the syringe barrel. In this embodiment, distal end 63 of the syringe barrel includes an elongate frusto-conically shaped tip having a passageway therethrough which provides the fluid path between the cannula and the chamber. The frusto-conically shaped tip of the barrel tip frictionally engages a frusto-conically shaped cavity of the needle hub. The distal end of the syringe barrel also includes a locking luer-type collar 68 concentrically surrounding the tip. The luer-collar has an array of internal threads which may engage the needle hub to hold it securely to the syringe barrel. For the purpose of drawing fluid into and out of chamber 67 the hypodermic syringe includes an elongate plunger rod 70 having a distal end 71 and a stopper 73 which is in fluid-tight slidable engagement with the interior of the chamber. It is important to note that it is within the scope of the present invention to include various hub configurations for attaching to a wide variety of medical or fluid-handling devices. The hub configuration described hereinabove, having a frusto-conically shaped interior cavity, reflects one of these many possibilities. Many syringes, fluid handling devices, such as stopcocks and adapters, and other fluid handling devices contain luer slip and locking luer-type fittings to which a hub having a frusto-conically shaped interior cavity will properly engage.

It is also within the purview of the present invention to provide a needle shield assembly wherein the hub is integrally molded with the syringe barrel and the base member is attached to the syringe barrel.

Figure 2:
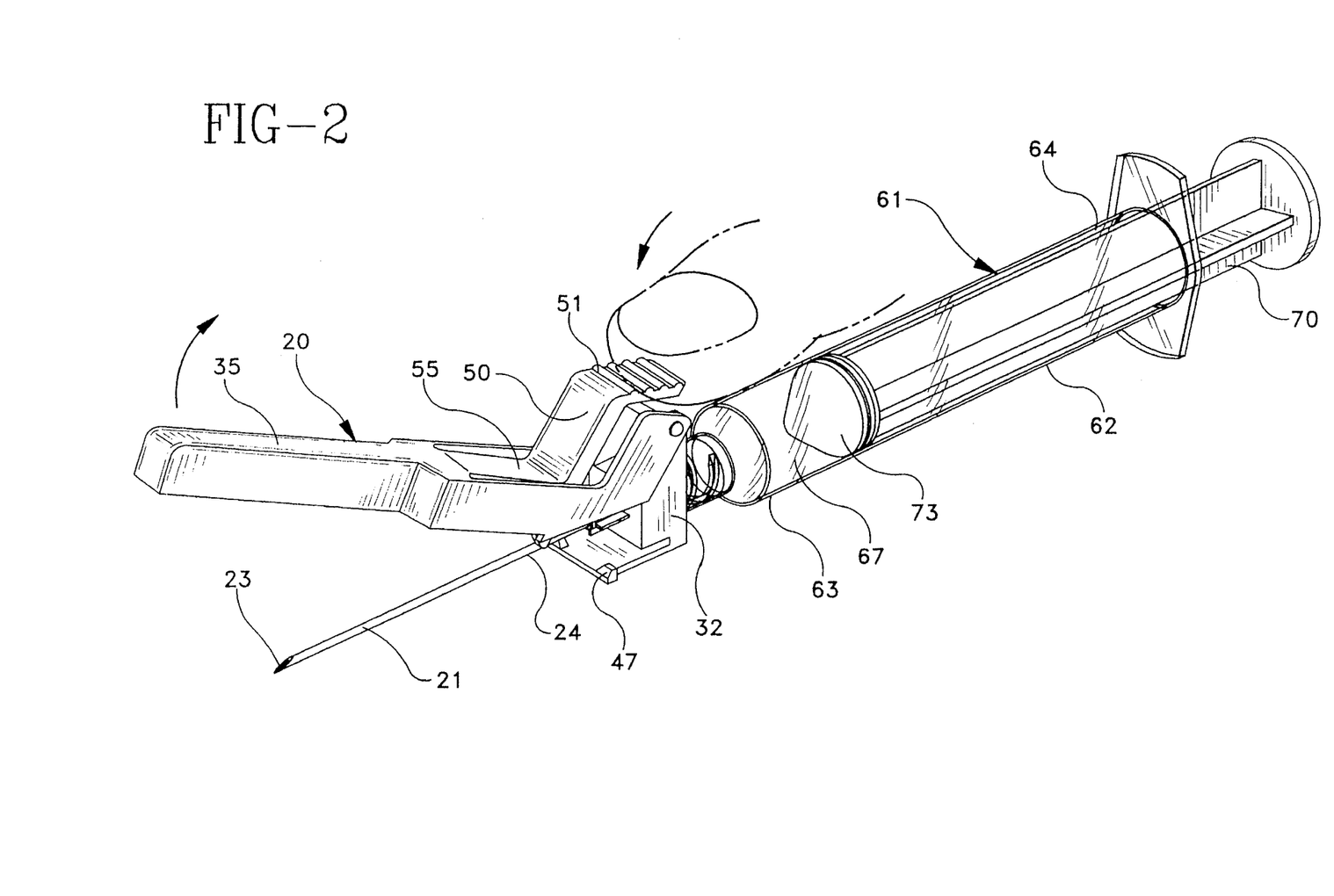
FIG. 2 is a perspective view of the needle shield assembly and syringe of FIG. 1 illustrating the needle shield being single-handedly unlocked and moved toward a needle exposing position.

The needle shield assembly of the present invention also includes means for releasably retaining the needle shield in the second needle exposing position. The second needle exposing position can be any position which exposes the distal end of the needle cannula. In FIG. 2 this position is illustrated with the needle shield at approximately a 90° angle with respect to longitudinal axis 24 of the needle cannula. In FIG. 4 the second position is illustrated with the needle shield at approximately 180° or parallel, with longitudinal axis 24 of the needle cannula. In this preferred embodiment the means for releasably retaining includes inwardly directed projections 74 on the needle shield and recesses 75 and 76 in the base member. When the needle shield is at an angle which is approximately perpendicular or 90° from the longitudinal axis of the needle cannula projection 74 engages recess 75 to releasably retain the needle shield in that position. The retention force provided by projection 74 and recess 75 can be overcome by applying additional rotational force to the needle shield. Also, when the needle shield is rotated approximately 180° from the needle cannula, as illustrated in FIG. 4, projection 74 engages recess 76 to releasably retain the needle shield in that position. Again, the needle shield can be moved back to the first needle protecting position by applying sufficient force to overcome resistance of projection 74 as it engages recess 76.

Figure 15:
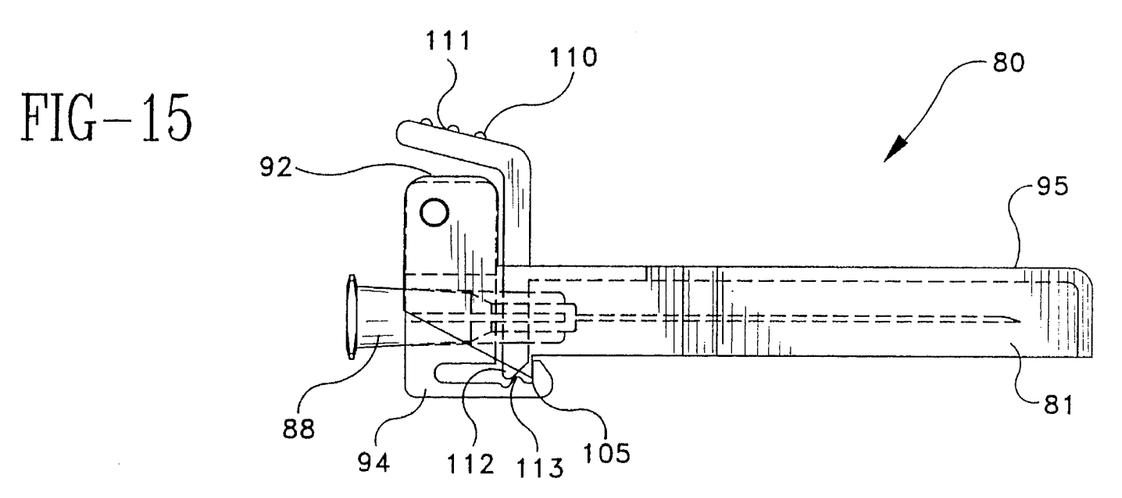
FIG. 15 is a side elevational view of an alternative embodiment of the needle shield assembly of the present invention.
Figure 16:
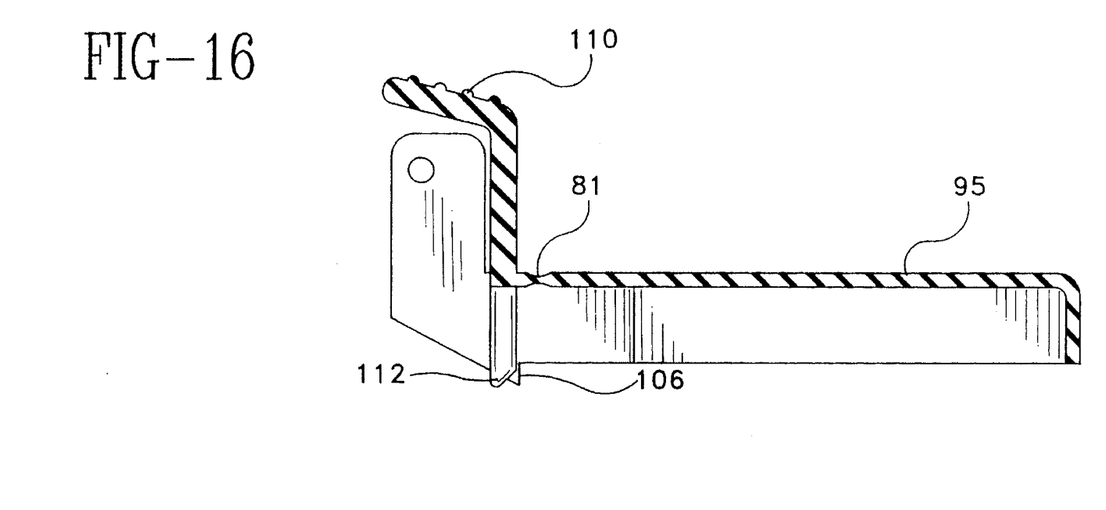
FIG. 16 is a cross-sectional view of the needle shield of the needle shield assembly of FIG. 15.

FIGS. 15 and 16 illustrate an alternative embodiment of the present invention. This embodiment is substantially similar in function to the embodiment of FIGS. 1–14 except for the structure providing the movable relationship between the needle shield and the activating member, and the shape of the contact surface on the locking arm. In particular, like the needle shield assembly of FIGS. 1–14, alternative needle shield assembly 80 includes a needle cannula 81, a hub 88, a base member 92 and an elongate needle shield 95. Needle shield 95 includes an activating member 110 movably connected to the needle shield having an outwardly facing finger pad 111 and a tip portion 112 located on the opposite side of the needle cannula from the finger pad when the needle shield is in the first needle protecting position as illustrated in FIG. 15. The movable relationship between needle shield 95 and activating member 50 is achieved through living hinge 81 which is integrally molded at the juncture of the activating member and the needle shield which allows the activating member to pivot with respect to the needle shield at hinge 81. It is within the purview of the instant invention to include any hinge structure, including a mechanical hinge, to achieve this relationship. As with the embodiment of FIGS. 1–14, the activating member is positioned so that digital pressure applied to the finger pad causes the tip portion of the activating member to push against a deflectable locking arm 94 of the base member and deflect the locking member so that latch surface 106 on the needle shield disengages latch surface 105 on the deflectable locking arm.

Figure 17:
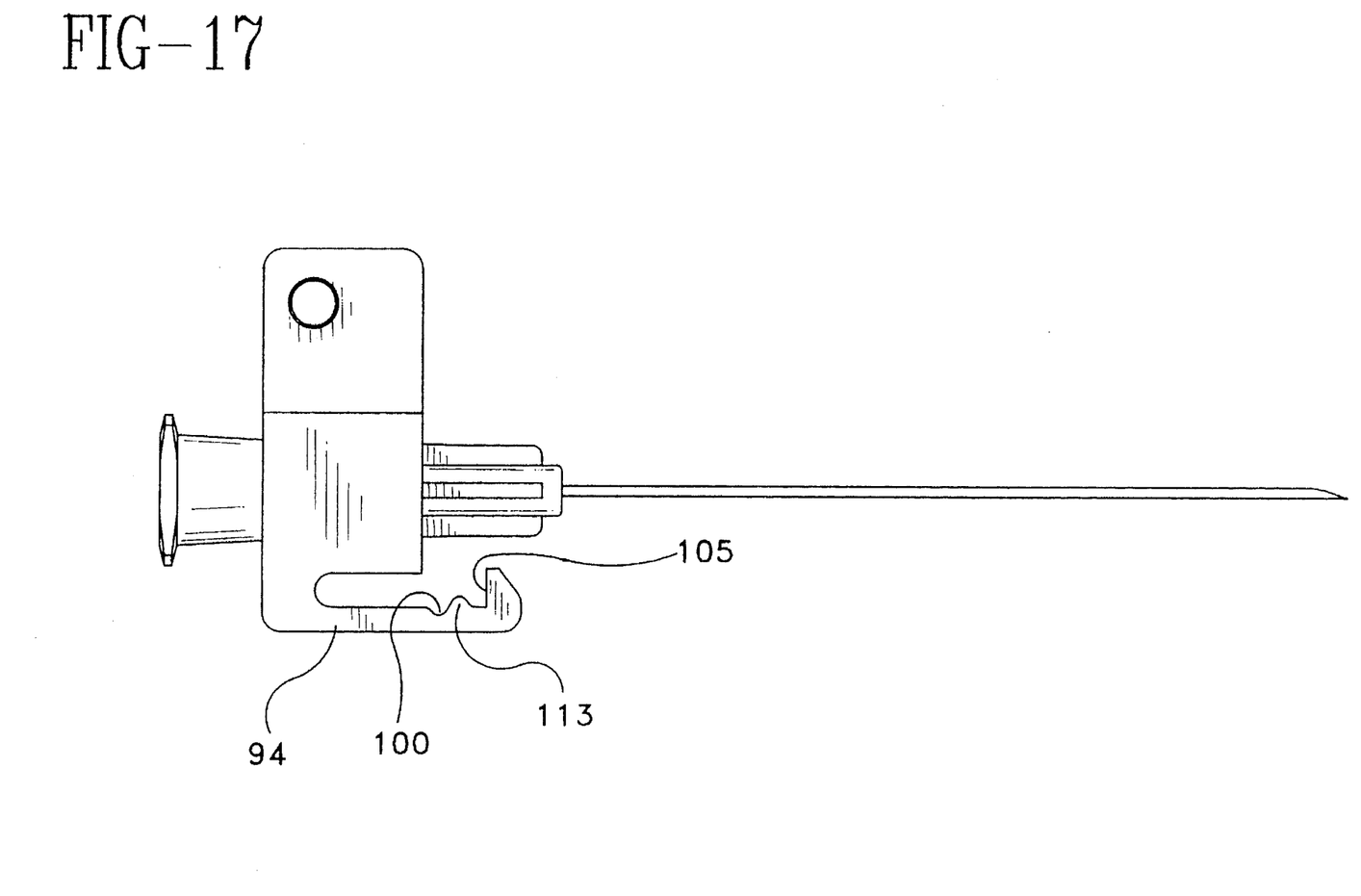
FIG. 17 is a side elevational view of the assembly of the needle cannula, hub and base member of the needle shield assembly of FIG. 15.

The larger the contact area between latch surface 105 and latch surface 106, the stronger the locking engagement between the base member and the needle shield to lock the needle shield in the first needle protecting position. The more the latch surfaces overlap the more the deflectable locking wall must be deflected to disengage the locking surfaces to unlock the needle shield. To provide additional deflection of the deflectable locking arm, the tip portion of the activating member or the contact surface on the locking arm which contacts the tip portion can be given a cam-like profile to magnify the deflection of the locking arm with respect to the movement of the tip portion of the activating member. In this embodiment, contact surface 113 is provided with a convexly shaped cam surface to magnify the response of the deflectable locking arm with respect to the motion of tip portion 112 over cam surface 113. The cam surface can also include a concavely shaped portion such as semi-circularly shaped portion 100 to hold the tip portion 112 of the activating member while the needle shield is in the first locked position. This will keep the tip portion 112 from moving away from the cam surface during normal use and will give the outwardly facing finger pad a more firm feel.

Figure 18:
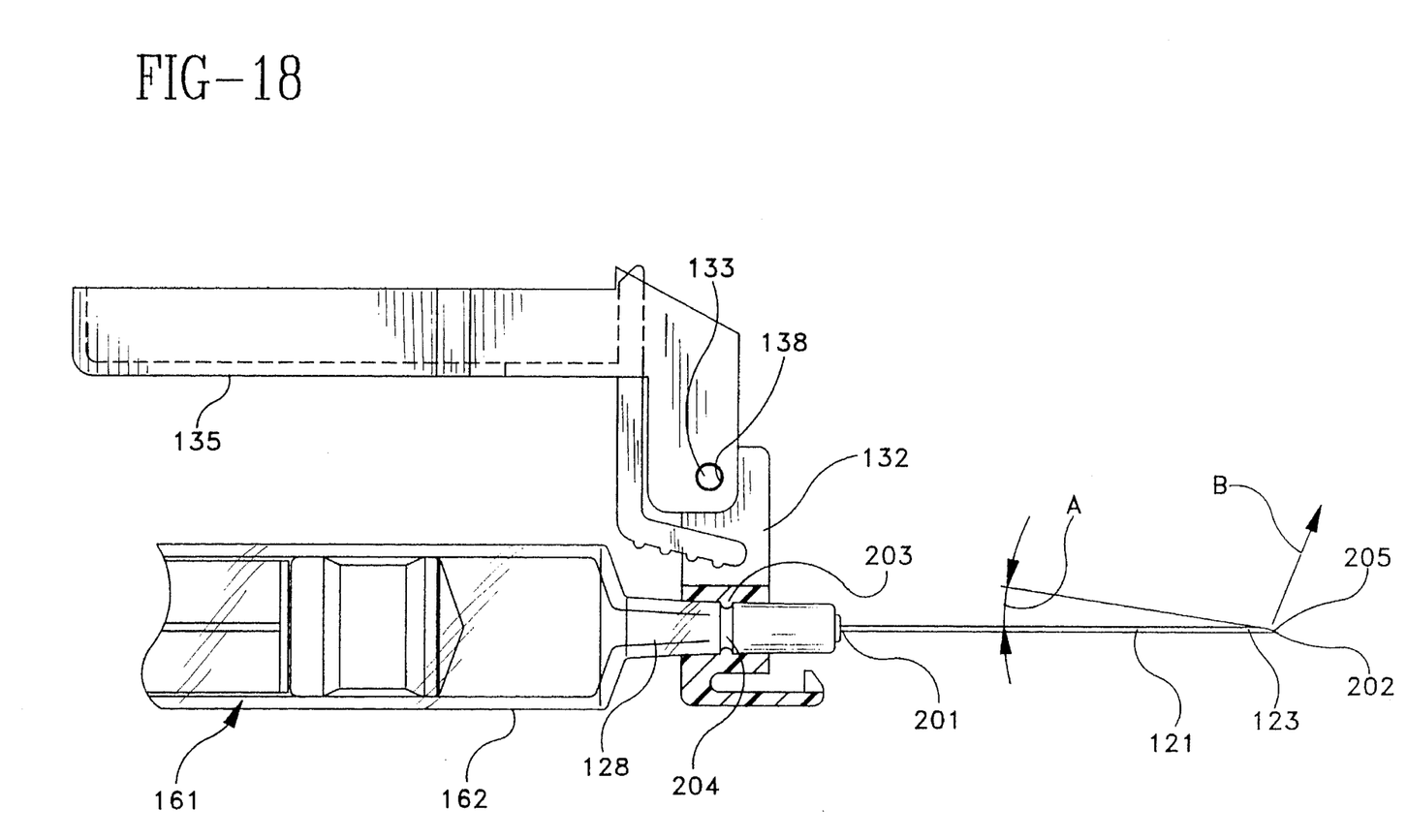
FIG. 18 is a side elevational view of an alternate embodiment of the needle shield assembly of the present invention.

FIG. 18 illustrates an alternate embodiment of the present invention which is similar to the embodiment of FIGS. 1–14 except that hub 128 is integrally formed with syringe barrel 162 of hypodermic syringe 161, and base member 132 is rotationally connected to hub 128. As in the embodiment of FIGS. 1–14, the needle shield assembly of the present embodiment includes an elongate needle shield 135 hingedly attached to base member 132 through the action of hinged pins 133 on the base member and hinge holes 138 in the needle shield. Needle cannula 121 is connected to hub 128 using an adhesive 201, such as epoxy, or by other suitable means. Distal end 123 of the needle cannula includes a sharp tip 202 which is sharpened to a bevel shape having a bevel surface 205 oriented at angle A. Bevel surface 205 faces direction B. Base member 132 is rotationally engaged with the hub in a snap-fit arrangement involving the engagement of inwardly facing annular rib 203 on the base member and annular recess 204 on the hub. The hub and the base member are dimensioned so that the base member will tightly fit the hub and remain in position but will allow rotation of the base member around the hub by applying a rotational force sufficient to overcome the frictional fit between the base member and the hub. There are numerous structural configurations that can be used to provide a rotational connection between the base member of the hub, such as tight threads, a ratchet structure, detents and the like. The structure described herein to provide for rotational connection between the base member and the hub is merely representative of these many possibilities. This is an important feature of the present embodiment because when injecting medication into a patient's vein it is desirable to have the bevel surface of the needle cannula facing upwardly as illustrated in FIG. 18. This orientation of the needle makes it easier to insert the needle into the patient's vein. Accordingly, it is desirable to have bevel surface 205 facing the same side of base member 132 as needle shield 135 when the needle shield is in the second needle exposing position, as best illustrated in FIG. 18, so that the needle shield does not interfere with positioning the syringe close to the patient's body, for example, the patient's arm, when attempting to gain easy access into a vein. The needle shield can be positioned on the same side of the syringe as the bevel surface by designing the elements so that the assembly of the needle shield assembly to the syringe barrel achieves this result or by providing adjustable components, such as in the embodiment of FIG. 18, where the base member can be rotated to the optimum position with respect to the needle cannula.

What is claimed:

1. A needle shield assembly having a releasable lock comprising:

a needle cannula having a proximal end, a distal end and a lumen therethrough;

a hub having a proximal end for connecting to a medical instrument and a distal end connected to said proximal end of said needle cannula;

a base member connected to said hub and including a deflectable locking arm having a latch surface, an elongate needle shield having a distal end and a proximal end hingedly connected to said base member, said needle shield having a longitudinal opening therein, said needle shield capable of rotating back and forth between a first needle protecting position wherein said needle cannula is within said longitudinal opening of said needle shield to a second position exposing at least the distal end of said needle cannula, said needle shield including a latch surface positioned to engage said latch surface of said base member when said needle shield is in said first needle protecting position for locking said needle shield in said first position, said needle shield including an activating member movably connected to said needle shield having an outwardly facing finger pad and a tip portion located on the opposite side of said cannula from said finger pad when said needle shield is in said first position, said activating member being positioned so that digital pressure applied to said finger pad causes said tip portion of said activating member to push against said locking arm of said base member and deflect said locking arm so that said latch surface of said locking arm disengages said latch surface of said needle shield and so that continued digital pressure on said finger pad causes said needle shield to rotate toward the side of said needle shield containing said finger pad, from said first needle shielding position to said second needle exposing position, said deflectable locking arm and said needle shield being configured so that rotation of said needle shield from said second position to said first position causes said locking surface of said locking arm and said locking surface on said needle shield to engage to lock said needle shield in said first position.

2. The needle shield assembly of claim 1 wherein said needle shield includes a proximally directed cantilever arm connected to said activating member at its free end so that digital pressure applied to said finger pad causes said cantilever arm to deflect in a direction toward said deflectable locking arm allowing said tip portion of said activating member to deflect said deflectable locking arm and disengage said locking surfaces.

3. The needle shield assembly of claim 1 including a hinge connecting said activating member to said needle shield.

4. The needle shield assembly of claim 1 wherein said deflectable locking arm includes a cam surface for said tip portion to contact for disengaging said latch surface of said needle shield from said latch surface of said locking arm.

5. The needle shield assembly of claim 4 wherein said cam surface includes a concavely shaped portion to contain said tip portion when said needle shield is in said first position.

6. The needle shield assembly of claim 1 further including means for releasably retaining said needle shield in said second needle exposing position.

7. The needle shield assembly of claim 6 wherein said second needle exposing position of said needle shield is about 90° from first position of said needle shield.

8. The needle shield assembly of claim 6 wherein said second needle exposing position of said needle shield is about 180° from said first position of said needle shield.

9. The needle shield assembly of claim 6 wherein said means for releasably retaining said needle shield in said second position includes a projection on said needle shield and a recess in said base member sized and shaped to frictionally engage said projection on said needle shield.

10. The needle shield assembly of claim 1 wherein said distal end of said needle cannula includes a sharp tip.

11. The needle shield assembly of claim 10 wherein said sharp tip is bevel-shaped having a bevel surface.

12. The needle shield assembly of claim 11 wherein said bevel surface faces the same side of said base member as said needle shield when said needle shield is in said second needle exposing position.

13. The needle shield assembly of claim 1 wherein said base member is rotationally connected to said hub so that said base member can be rotated around said hub.

14. The needle shield of claim 1 wherein said hub and said base member are a unitary one-piece structure.

15. The needle shield assembly of claim 1 further including a syringe barrel having a distal end, a proximal end and a circular side wall therebetween defining a chamber for retaining fluid, said distal end of said syringe barrel being connected to said hub so that said lumen of said needle cannula is in fluid communication with said chamber.

16. The needle shield assembly of claim 15 wherein said hub and said syringe barrel are of a unitary one-piece construction.

17. A needle shield assembly having a releasable lock comprising:

a needle cannula having a proximal end, a distal end and a lumen therethrough;

a hub having a proximal end for connecting to a medical instrument and a distal end connected to the proximal end of said needle cannula;

a base member connected to said hub and including a deflectable locking arm having a latch surface, an elongate needle shield having a distal end and a proximal end hingedly connected to said base member, said needle shield having a longitudinal opening therein, said needle shield capable of rotating back and forth between a first needle protecting position wherein said needle cannula is within said longitudinal opening of said needle shield to a second position exposing at least the distal end of said needle cannula, said needle shield including a latch surface positioned to engage said latch surface of said base member when said needle shield is in said first needle protecting position for locking said needle shield in said first position, said needle shield including activating means having an outwardly facing finger pad for disengaging said latch surface of said locking arm and said latch surface of said needle shield and for rotating said needle shield from said first needle shielding position to said second needle exposing position upon the application of digital pressure to said finger pad.

18. The needle shield assembly of claim 17 further including means for automatically engaging said latch surface of said locking arm and said latch surface of said needle shield when said needle shield is rotated from said second needle exposing position to said first needle shielding position.

19. The needle shield assembly of claim 17 wherein said activating means includes an activating member movably connected to said needle shield including said outwardly facing finger pad and a tip portion located on the opposite side of the cannula from said finger pad when said needle shield is in said first position.

20. The needle shield assembly of claim 17 further including means for releasably retaining said needle shield in said second needle exposing position.

21. The needle shield assembly of claim 17 further including a syringe barrel having a distal end, a proximal end and a circular side wall therebetween defining a chamber for retaining fluid, said distal end of said syringe barrel being connected to said hub so that said lumen of said needle cannula is in fluid communication with said chamber.

* * * * *